US009358318B2

(12) United States Patent
Gorman et al.

(10) Patent No.: US 9,358,318 B2
(45) Date of Patent: *Jun. 7, 2016

(54) METHOD OF MAKING A REINFORCED ABSORBABLE MULTILAYERED HEMOSTATIC WOUND DRESSING

(75) Inventors: Anne Jessica Gorman, Hightstown, NJ (US); Sanyog Manohar Pendharkar, Edison, NJ (US)

(73) Assignees: Ethicon, Inc., Somerville, NJ (US); Omrix Biopharmaceutical, Inc., Rhode-St-Genese (BE)

( * ) Notice: Subject to any disclaimer, the term of this patent is extended or adjusted under 35 U.S.C. 154(b) by 1113 days.

This patent is subject to a terminal disclaimer.

(21) Appl. No.: 12/400,522

(22) Filed: Mar. 9, 2009

(65) Prior Publication Data

US 2009/0246238 A1    Oct. 1, 2009

Related U.S. Application Data

(62) Division of application No. 11/400,849, filed on Apr. 10, 2006.

(51) Int. Cl.
| A61K 9/70 | (2006.01) |
| A61F 13/00 | (2006.01) |
| A61L 15/32 | (2006.01) |
| A61L 15/26 | (2006.01) |
| A61L 15/28 | (2006.01) |
| A61L 15/44 | (2006.01) |
| A61L 15/64 | (2006.01) |

(52) U.S. Cl.
CPC . *A61L 15/32* (2013.01); *A61K 9/70* (2013.01); *A61K 9/7007* (2013.01); *A61L 15/26* (2013.01); *A61L 15/28* (2013.01); *A61L 15/44* (2013.01); *A61L 15/64* (2013.01); *A61L 2300/418* (2013.01)

(58) Field of Classification Search
None
See application file for complete search history.

(56) References Cited

U.S. PATENT DOCUMENTS

| 2,517,772 A | 8/1950 | Doub et al. |
| 2,772,999 A | 12/1956 | Masci et al. |
| 2,773,000 A | 12/1956 | Masci et al. |
| 2,914,444 A | 11/1959 | Smith |
| 3,113,568 A | 12/1963 | Robins |
| 3,122,479 A | 2/1964 | Smith |
| 3,328,529 A | 6/1967 | Heald |
| 3,364,200 A | 1/1968 | Ashton et al. |
| 3,868,955 A | 3/1975 | Steiger et al. |
| 3,875,937 A | 4/1975 | Schmitt et al. |
| 4,128,612 A | 12/1978 | Roth |
| 4,176,664 A | 12/1979 | Kalish |
| 4,214,582 A | 7/1980 | Patel |
| 4,265,233 A | 5/1981 | Sugitachi et al. |
| 4,289,824 A | 9/1981 | Smith |
| 4,334,530 A | 6/1982 | Hassell |
| 4,347,841 A | 9/1982 | Benyo et al. |
| 4,366,169 A | 12/1982 | White |
| 4,407,787 A | 10/1983 | Stemberger |
| 4,427,650 A | 1/1984 | Stroetmann |
| 4,427,651 A * | 1/1984 | Stroetmann ..................... 424/46 |
| 4,442,655 A | 4/1984 | Stroetmann |
| 4,453,939 A | 6/1984 | Zimmerman et al. |
| 4,534,349 A | 8/1985 | Barrows |
| 4,543,410 A | 9/1985 | Cruz, Jr. |
| 4,600,574 A | 7/1986 | Lindner |
| 4,616,644 A | 10/1986 | Saferstein et al. |
| 4,626,253 A | 12/1986 | Broadnax |
| 4,655,211 A | 4/1987 | Sakamoto et al. |
| 4,704,113 A | 11/1987 | Schoots |
| 4,752,466 A | 6/1988 | Saferstein et al. |
| 4,769,028 A | 9/1988 | Hoffmann et al. |
| 4,840,626 A | 6/1989 | Linsky |
| 4,858,604 A | 8/1989 | Konishi |
| 4,882,162 A | 11/1989 | Ikada et al. |
| 4,902,281 A | 2/1990 | Avoy |
| 4,909,243 A | 3/1990 | Frank et al. |
| 4,948,540 A | 8/1990 | Nigam |
| 5,002,551 A | 3/1991 | Linsky et al. |
| 5,007,916 A | 4/1991 | Linsky et al. |
| 5,026,589 A | 6/1991 | Schechtman |
| 5,037,692 A | 8/1991 | Miyazaki et al. |
| 5,055,316 A | 10/1991 | Hoffman et al. |
| 5,059,189 A | 10/1991 | Cilento et al. |
| 5,067,964 A | 11/1991 | Richmond et al. |
| 5,098,417 A | 3/1992 | Yamazaki et al. |
| 5,099,003 A | 3/1992 | Kotitschke et al. |
| 5,134,229 A | 7/1992 | Saferstein et al. |
| 5,141,516 A | 8/1992 | Detweiler |

(Continued)

FOREIGN PATENT DOCUMENTS

| AU | 2005295365 | 4/2006 |
| AU | 2005295367 | 4/2006 |

(Continued)

OTHER PUBLICATIONS

JS Textile Humidification webpage (http://www.jshumidifiers.com/textiles-42-application; available at least by Jul. 30, 2004).*
Arand, A.G. et al 'Intraoperative Chemical Hemostasis in Neurosurgery' Neurosurgery, vol. 18, No. 2 pp. 223-233 (1986).
ASTM (American Society for Testing and Materials), Designation: E11-87 'Standard Specification for Wire-Cloth Sieves for Testing Purposes' pp. 13-16 (1987).
Davidson, G.F. '7—The Properties of the Oxycelluloses Formed in the Early Stages of the Oxidation of Cotton Cellulose by Periodic Acid and Metaperiodate' The Journal of the Textile Institute-Transactions pp. T81-T96 (Jul. 1940).

(Continued)

*Primary Examiner* — Kevin S Orwig
(74) *Attorney, Agent, or Firm* — David R. Crichton

(57) ABSTRACT

The present invention is directed to a reinforced absorbable multilayered hemostatic wound dressing comprising a first absorbable nonwoven fabric, a second absorbable woven or knitted fabric, thrombin and/or fibrinogen.

20 Claims, 1 Drawing Sheet

(56) References Cited

U.S. PATENT DOCUMENTS

| | | |
|---|---|---|
| 5,180,398 A | 1/1993 | Boardman et al. |
| 5,223,420 A | 6/1993 | Rabaud et al. |
| 5,238,685 A | 8/1993 | Wren |
| 5,263,629 A | 11/1993 | Trumbull et al. |
| 5,270,300 A | 12/1993 | Hunziker |
| 5,272,074 A | 12/1993 | Rubens |
| 5,330,974 A | 7/1994 | Pines et al. |
| 5,393,594 A | 2/1995 | Koyfman et al. |
| 5,395,923 A | 3/1995 | Bui-Khac et al. |
| 5,409,703 A | 4/1995 | McAnalley et al. |
| 5,573,757 A * | 11/1996 | Riess et al. .................. 424/78.02 |
| 5,593,441 A | 1/1997 | Lichtenstein et al. |
| 5,643,596 A | 7/1997 | Pruss et al. |
| 5,645,849 A | 7/1997 | Pruss et al. |
| 5,683,794 A | 11/1997 | Wadsworth et al. |
| 5,686,090 A | 11/1997 | Schilder et al. |
| 5,795,584 A | 8/1998 | Totakura et al. |
| 5,821,343 A | 10/1998 | Keogh |
| 5,843,057 A | 12/1998 | McCormack |
| 5,866,165 A | 2/1999 | Liu et al. |
| 5,914,118 A | 6/1999 | Yamamura et al. |
| 5,925,552 A | 7/1999 | Keogh et al. |
| 5,945,319 A | 8/1999 | Keogh |
| 5,972,366 A | 10/1999 | Haynes et al. |
| 6,017,741 A | 1/2000 | Keogh |
| 6,054,122 A | 4/2000 | MacPhee et al. |
| 6,056,970 A | 5/2000 | Greenawalt et al. |
| 6,114,495 A | 9/2000 | Kolstad et al. |
| 6,121,232 A | 9/2000 | Nur et al. |
| 6,165,217 A | 12/2000 | Hayes |
| 6,214,808 B1 | 4/2001 | Soe et al. |
| 6,261,679 B1 | 7/2001 | Chen et al. |
| 6,306,424 B1 | 10/2001 | Vyakamam et al. |
| 6,333,029 B1 | 12/2001 | Vyakamam et al. |
| 6,365,149 B2 | 4/2002 | Vyakamam et al. |
| 6,500,777 B1 | 12/2002 | Wiseman et al. |
| 6,585,957 B1 | 7/2003 | Adjei et al. |
| 6,613,324 B1 | 9/2003 | Blomback et al. |
| 6,649,162 B1 | 11/2003 | Biering et al. |
| 6,653,520 B1 | 11/2003 | Mouton |
| 6,733,774 B2 | 5/2004 | Stimmeder |
| 6,762,336 B1 | 7/2004 | MacPhee et al. |
| 7,179,833 B2 | 2/2007 | Dubuffet et al. |
| 7,252,837 B2 | 8/2007 | Guo et al. |
| 7,279,177 B2 | 10/2007 | Looney et al. |
| 7,572,769 B2 | 8/2009 | Rapp et al. |
| 2001/0025154 A1 | 9/2001 | Rapp |
| 2002/0012693 A1 | 1/2002 | Cohen et al. |
| 2002/0085994 A1 | 7/2002 | Ceres et al. |
| 2002/0120348 A1 | 8/2002 | Melican et al. |
| 2002/0173213 A1 | 11/2002 | Chu et al. |
| 2002/0187194 A1 | 12/2002 | Stimmeder |
| 2002/0197302 A1 | 12/2002 | Cochrum et al. |
| 2003/0073663 A1 | 4/2003 | Wisemann et al. |
| 2003/0118651 A1 | 6/2003 | Jampani et al. |
| 2003/0171052 A1 | 9/2003 | Bansal et al. |
| 2004/0001879 A1 | 1/2004 | Guo et al. |
| 2004/0005350 A1 | 1/2004 | Looney et al. |
| 2004/0064878 A1 | 4/2004 | Walsh |
| 2004/0078077 A1 | 4/2004 | Binette et al. |
| 2004/0101546 A1 | 5/2004 | Gorman et al. |
| 2004/0101547 A1 | 5/2004 | Pendharkar et al. |
| 2004/0101548 A1 | 5/2004 | Pendharkar et al. |
| 2004/0106344 A1 | 6/2004 | Looney et al. |
| 2004/0120993 A1 | 6/2004 | Zhang et al. |
| 2004/0137033 A1 | 7/2004 | Calhoun et al. |
| 2004/0193088 A1 | 9/2004 | Looney et al. |
| 2004/0241212 A1 | 12/2004 | Pendharkar et al. |
| 2004/0243043 A1 | 12/2004 | McCarthy et al. |
| 2004/0265371 A1 | 12/2004 | Looney et al. |
| 2005/0008632 A1 * | 1/2005 | Stimmeder .................. 424/94.64 |
| 2005/0123588 A1 | 6/2005 | Zhu et al. |
| 2006/0051340 A1 | 3/2006 | Uchida et al. |
| 2006/0084338 A1 | 4/2006 | Shetty et al. |
| 2006/0127460 A1 | 6/2006 | Uchida et al. |
| 2006/0258995 A1 | 11/2006 | Pendharkar et al. |
| 2008/0003272 A1 | 1/2008 | Rapp et al. |
| 2008/0206298 A1 | 8/2008 | Burkinshaw et al. |

FOREIGN PATENT DOCUMENTS

| | | | |
|---|---|---|---|
| AU | 2005295368 | 4/2006 | |
| AU | 2006341588 | 10/2007 | |
| CA | 1097898 | 3/1981 | |
| CA | 2363916 | * 7/2000 | ............. A61L 24/10 |
| CA | 2433977 | 6/2004 | |
| CA | 2513319 | 8/2004 | |
| CN | 1507358 | 6/2004 | |
| CN | 1531976 | 9/2004 | |
| CN | 101084021 | 12/2007 | |
| CS | 217243 | 3/1985 | |
| CS | 235108 | 2/1987 | |
| CS | 238016 | 10/1987 | |
| EP | 0092999 | 11/1983 | |
| EP | 0109197 | 5/1984 | |
| EP | 59265 | 8/1985 | |
| EP | 0213563 | 3/1987 | |
| EP | 0216378 | 4/1987 | |
| EP | 0090997 | 10/1989 | |
| EP | 0361842 | 4/1990 | |
| EP | 0372969 | 6/1990 | |
| EP | 0431479 | 6/1991 | |
| EP | 0177064 | 8/1991 | |
| EP | 0468114 | 1/1992 | |
| EP | 0338829 | 8/1993 | |
| EP | 0610731 | 8/1994 | |
| EP | 0636378 | 2/1995 | |
| EP | 0647734 | 4/1995 | |
| EP | 0507807 | 5/1997 | |
| EP | 0506775 | 8/1997 | |
| EP | 0815879 | 1/1998 | |
| EP | 0878179 | 11/1998 | |
| EP | 0815881 | 5/2003 | |
| EP | 1400624 | 3/2004 | |
| EP | 1424086 | 6/2004 | |
| EP | 1424087 | 6/2004 | |
| EP | 1430911 | 6/2004 | |
| EP | 1172115 | 6/2005 | |
| EP | 1574229 | 9/2005 | |
| EP | 1378255 | 1/2007 | |
| EP | 1462122 | 4/2011 | |
| FR | 2663229 | 12/1991 | |
| FR | 2663841 | 1/1992 | |
| GB | 0942305 | 11/1963 | |
| GB | 0983073 | 2/1965 | |
| GB | 1183951 | 3/1970 | |
| GB | 2314840 | 1/1998 | |
| GB | 2314842 | 1/1998 | |
| GB | 2344519 | 6/2000 | |
| IN | 159332 | 5/1987 | |
| IN | 0362/KOL/2003 | 6/2003 | |
| JP | 60-087225 | 5/1985 | |
| JP | 60872250 | 5/1985 | |
| JP | 61-200837 | 9/1986 | |
| JP | 62-047364 | 3/1987 | |
| JP | 63-103643 | 7/1988 | |
| JP | 01-271513 | 10/1989 | |
| JP | 04-316673 | 11/1992 | |
| JP | 07-031672 | 2/1995 | |
| JP | 07-041731 | 2/1995 | |
| JP | 07-194689 | 8/1995 | |
| JP | 07-207560 | 8/1995 | |
| JP | 08-302553 | 11/1996 | |
| JP | 9-504719 | 5/1997 | |
| JP | 10-510183 | 10/1998 | |
| JP | 11-17041 3 | 6/1999 | |
| JP | 2000-513258 | 10/2000 | |
| JP | 2001-231847 | 8/2001 | |
| JP | 2001-238900 | 9/2001 | |
| JP | 2002-017764 | 1/2002 | |
| JP | 2002-533164 | 10/2002 | |
| JP | 2004-136097 | 5/2004 | |
| JP | 2004-160182 | 6/2004 | |
| JP | 2004-174221 | 6/2004 | |

(56) References Cited

FOREIGN PATENT DOCUMENTS

| | | | | |
|---|---|---|---|---|
| JP | 2004-174223 | 6/2004 | | |
| JP | 2004-232160 | 8/2004 | | |
| JP | 2005-015484 | 1/2005 | | |
| JP | 2005-046601 | 2/2005 | | |
| JP | 2005-169103 | 6/2005 | | |
| JP | 2007-255830 | 10/2007 | | |
| JP | 2007-537973 | 12/2007 | | |
| JP | 2007-537974 | 12/2007 | | |
| JP | 2008-516736 | 5/2008 | | |
| JP | 2008-516819 | 5/2008 | | |
| KR | 10-1995-0009487 | 8/1995 | | |
| KR | 10-1995-0008911 | 2/2001 | | |
| KR | 2004-0055564 | 6/2004 | | |
| KR | 2005-0100626 | 10/2005 | | |
| RU | 2146264 | 3/2000 | | |
| RU | 2235539 | 9/2004 | | |
| TW | 2004/18530 | 10/2004 | | |
| WO | WO 91/01762 | 2/1991 | | |
| WO | WO 91/08726 | 6/1991 | | |
| WO | WO 91/16063 | 10/1991 | | |
| WO | WO 91/18571 | 12/1991 | | |
| WO | WO 92/13495 | 8/1992 | | |
| WO | WO 92/15341 | 9/1992 | | |
| WO | WO 93/10731 | * | 6/1993 | .............. A61F 13/00 |
| WO | WO 94/11022 | 5/1994 | | |
| WO | WO 95/12371 | 5/1995 | | |
| WO | WO 96/16643 | 6/1996 | | |
| WO | WO 96/40033 | 12/1996 | | |
| WO | 98/00180 | 1/1998 | | |
| WO | WO 98/00180 | 1/1998 | | |
| WO | WO 98/00446 | 1/1998 | | |
| WO | WO 98/33479 | 8/1998 | | |
| WO | WO 99/01166 | 1/1999 | | |
| WO | WO 00/01166 | 1/2000 | | |
| WO | WO 01/22059 | 3/2001 | | |
| WO | WO 01/23653 | 4/2001 | | |
| WO | WO 02/02155 | 1/2002 | | |
| WO | WO 02/22059 | 3/2002 | | |
| WO | WO 02/058750 | 8/2002 | | |
| WO | WO 02/095019 | 11/2002 | | |
| WO | WO 03/020191 | 3/2003 | | |
| WO | WO 2004/043503 | 5/2004 | | |
| WO | WO 2004/064878 | 8/2004 | | |
| WO | 2004/106363 | 12/2004 | | |
| WO | WO 2006/044879 | 4/2006 | | |
| WO | WO 2006/044882 | 4/2006 | | |
| WO | 2007/117237 | 10/2007 | | |

OTHER PUBLICATIONS

Edwards, J.V. et al 'Modified Cotton Gauze Dressing that Selectively Absorb Neutrophilelastase Activity in Solution' Wound Repair and Regeneration, vol. 9, No. 1, pp. 50-58 (2001).
Encyclopedia of Polymer Science and Engineering, vol. 10, pp. 204-253 (1987).
Frantz, V.K. et al 'New Absorbable Hemostatic Agents' The Bulletin, vol. 22, pp. 102-110 (1946).
Frantz, V.K. et al 'Oxidized Cellulose-Absorbable Gauze (Cellulosic Acid)' Journal of American Medical Association, vol. 129 pp. 798-801 (1945).
Hercules Aqualon® Sodium Carboxymethylcellulose Product Specifications No. 4116-4, 1997.
Hercules Aqualon® Sodium Carboxymethylcellulose Physical and Chemical Properties 1995.
Jackson, E.L. et al 'Application of the Cleavage Type of Oxidation by Periodic Acid to Starch and Cellulose' Journal of American Chemistry Society, vol. 59 pp. 2049-2050 (1937).
Lucas, O.N. 'Inactivation of Thrombin by Oxidized Cellulose' Journal of Oral Therapeutics and Pharmacology, vol. 3 No. 4 pp. 262-268 (1967).
Matras, H. 'Fibrin Seal: The State of the Art' Journal of Oral Maxillofacial Surg., vol. 43, No. 8, pp. 605-611, 1985.
Singh, M. et al 'An Insulin Delivery System from Oxidized Cellulose' Journal of Biomedical Materials Research, vol. 15, pp. 655-661 (1981).
Sinha, T.J.M., et al 'Blood-Cellulosics Interactions' Biomat. Med. Dev. Art. Org. No. 12(3-4) pp. 273-287 (1984-1985).
Stillwell, R.L., et al '15. Oxidized Cellulose: Chemistry, Processing and Medical Applications' Handbook of Biodegradable Polymers, Edited by Domb et al pp. 291-306 (1997).
Turaev, A.D., et al 'Hemostatic Activity and Reabsorbability of Carboxymethyl Cellulose' Khim-Farm.Zh., 24(8) pp. 47-51 (1990 English Abstract).
International Search Report dated Jun. 13, 2006 for corresponding Appln. No. PCT/US2005/037403.
International Search Report dated Jun. 26, 2006 for corresponding Appln. No. PCT/US2005/037407.
International Search Report dated Jan. 11, 2007 for corresponding Appln. No. PCT/US2006/013282.
Chun, W., et al 'The Development and Current Situation of Polylactic Acid Fibers' (2005) Industrial Textiles, No. 7.
JS Textile Humidification webpage (http.//www.jshumidifiers.com/textiles-42-application; available at least by Jul. 30, 2004).
Adant, J. et la. "*Skin Grafting with Fibrin Glue in Burns*", Eur J Plast Surg, 16(6), 292-297 (Dec. 1993).
Bianucci, HC, "*Periodontal Healing of Canine Experimental Grade III Furcation Defects Treated With Autologous Fibrinogen and Resolut® Barrier Membrane*", Thesis, MS in Veterinary Medical Sci. Virginia Polytechnic Institute and State Univ. (May 26, 1998).
Brennan, M. "*Fibrin Glue*", Blood Reviews, 5(4), 240-244 (Dec. 1991).
Burnouf-Radosevich, M. et al. "*Biochemical and Physical Properties of a Solvent-Detergent-Treated Fibrin Glue*" Vox Sang, 58(2), 77-84 (1990).
Callender, S et al. "*Treatment of Menorrhagia with Tranexamic Acid. A Double-blind Trial*" Brit. Med. J., 4, 214-216 (1970).
Carless, PA, et al. "*Fibrin sealant use for minimising peri-operative allogeneic blood transfusion (Review)*" Cochrane Database of Systematic Reviews, Issue 1 (2003).
Chang, H. et al. "*Effects of Fibrin Glue on Hemostasis*" J Formosan Med Assoc, 91(6), 601-607 (Jun. 1992).
Gordon, AM et al. "*Clinical Trial of Epsilon-aminocaproic Acid in Severe Haemophilia*" Brit. Med. J., 1, 1632-1635 (1965).
Evans, LA et al. "*Current Applications of Fibrin Sealant in Urologic Surgery*" Int Braz J Urol, 32(2), 131-141 (Mar.-Apr. 2006).
Sundaram, CP et al. "*Evolution of hemostatic agents in surgical practice*" Indian J Urol., 26(3), 374-378 (Jul.-Sep. 2010).
Galanakis, I et al. "*A Review of Current Hemostatic Agents and Tissue Sealants Used in Laparoscopic Partial Nephrectomy*" Reviews in Urology, 13(3), 131-138 (2011).
Hauck, H. et al. "*Complicated Pneumothorax: Short- and Long-Term Results of Endoscopic Fibrin Pleurodesis*" World J of Surg, 15(1), 146-49 (Jan.-Feb. 1991).
Staindl, O, "*The Healing of Wounds and Scar Formation under the Influence of a Tissue Adhesion System with Fibrinogen, Thrombin, and Coagulation Factor XIII*" Arch. Otorhinolaryngol., 222, 241-245 (1979).
Furtmuller, R. et al. "*Tranexamic Acid, a Widely Used Antifibrinolytic Agent, Causes Convulsions by a gamma-Aminobutyric Acid A Receptor Antagonistic Effect*" J Pharm Experimental Therapeutics, 301(1), 168-73 (2002).
Levy, A. "*Unusual Reaction to Trasylol*" CMA Journal, 111, 1304 (letter to the editor), (1974).
Marchac, D et al. "*The Use of Sprayed Fibrin Glue for Face Lifts*" Eur J Plast Surg, 10, 139-143 (1987).
Marczell, A. et al. "*Partial Pancreaticoduodenectomy (Whipple Procedure) for Pancreatic Malignancy: Occlusion of a Non-Anastomosed Pancreatic Stump With Fibrin Sealant*" HPB Surgery, 5, 2561-260 (1992).
Miyakf, K. et al. "Clinical Application of a New Fibrin Adhesive (Tisseel) in Urologic Surgery" Acta Urologica Japonica, 31(2), 357-364 (Feb. 1985).
Ochsner, MG et al. "*Fibrin Glue as a Hemostatic Agent in Hepatic and Splenic Trauma*" J Trauma, 30(7), 884-887 (Jul. 1990).
Pellegrini, A. et al. "*Feline Generalized Epilepsy Induced by Tranexamic Acid (AMC)*" Epilepsia, 23(1), 35-45 (1982).
Petti, G. "Characteristics and Activity of Fibrin Glue" http://www.gustavopetti.it/HtmlInglese/collafibr.htm, 1987.

(56) References Cited

OTHER PUBLICATIONS

Scapinelli, R. "*Treatment of Fractures of the Humeral Capitulum Using Fibrin Sealant*" Arch Orthop and Trauma Surg, 109(4), 235-237 (Jun. 1990).
Shekarriz B. et al. "*The Use of Fibrin Sealant in Urology*" J Urol, 167, 1218-1225 (Mar. 2002).
Mintz, PD et al. "*Review: Fibrin Sealant: Clinical Use and the Development of the University of Virginia Tissue Adhesive Center*" Annals of Clinical & Laboratory Science, 31(1), 108-118 (2001).
Erdos, EG "*Hypotensive Peptides: Bradykinin, Kallidin, and Eledosin*" Advances in Pharmacology, 4, 12 (1966).
Van der Ham, A, et al "*Healing of Ischemic Colonic Anastomosis: Fibrin Sealant Does Not Improve Wound Healing*" Diseases of the Colon & Rectum, 35(9), 884-891 (Sep. 1992).
Verstraete, M "*Improve Wound Healing*", Diseases of the Colon & Rectum, vol. 35(9), pp. 884-91 (Sept. Haemostatic Drugs, 127-131 (1977).
Cox, S et al. "*Effect of Tranexamic Acid Incorporated in Fibrin Sealant Clots On the Cell Behavior of Neuronal and Nonneuronal Cells*" J Neuroscience Res, 72, 734-746 (2003).
Schlag, MG et al. "*Epileptic Seizures Following Cortical Application of Fibrin Sealants Containing Tranexamic Acid in Rats*" Acta Neurochir, 144, 63-69 (2002).
Schlag, MG et al. "*Convulsive Seizures Following Subdural Application of Fibrin Sealant Containing Tranexamic Acid in a Rat Model*" Neurosurgery, 47, 1463-1467 (2000).
Kheirabadi, BS et al. "*Development of Hemostatic Dressings for Use in Military Operations*" RTO-MP-HFM-109, pp. 1-12 (2004).
Schwartz, SI et al. "*Hemostasis, Surgical Bleeding, and Transfusion*" Ch. 3 in Principles of Surgery, 7th ed, McGraw hill Co, 77-100 (1999).
Chu, C.C. Dumitriu Ed., Polymeric Biomaterials, Chapter 19, Textile-based biomaterials for surgical application, (2002) 54 pages.
Miraftab, M. et al 'Advanced Wound-care Materials: Ultra High Absorbing Fibres made from Alginates Containing Branan Ferulate and Carboxymethyl Cellulose' J. Text. Inst. (2004) vol. 25 No. 1-6 pp. 341-348.
Young, S.T. et al 'Appearance of Oxidized Cellulose (Surgicel) on Postoperative CT Scans: Similarity to Postoperative Abscess' American Journal of Roentgenology vol. 160, No. 2 (1993) pp. 275-277.
International Preliminary Report on Patentability re: PCT/US2005/037403 dated Apr. 24, 2007.
International Preliminary Report on Patentability re: PCT/US2006/013282 dated Oct. 14, 2008.
AU Examiners First Report Issued by the Australian Patent Office in co-pending Australian Patent Application No. 2006341589 dated May 2, 2011.
AU Examiners Second Report Issued by the Australian Patent Office in co-pending Australian Patent Application No. 2006341589 dated Sep. 16, 2011.
CN Second Office Action Issued by the Chinese Patent Office (CIPO) in co-pending Chinese Patent Application No. 200580043617.0 filed Oct. 17, 2005.
European Search Report re: 08075829 dated Aug. 27, 2012.
European Search Report re: 14184308 dated Jan. 14, 2015.
EP Extended European Search Report Issued by the European Patent Office in co-pending EP Patent Application No. 11161264 dated May 31, 2011.
EP Extended European Search Report Issued by the European Patent Office in co-pending EP Patent Application No. 11161264 dated Jun. 9, 2011.
International Preliminary Report on Patentability re: PCT/US2005/037402 dated Apr. 24, 2007.
JP First Office Action Issued by the Japanese Patent Office in co-pending Japanese Patent Application No. 2007-537973 dated Mar. 29, 2011.
JP First Office Action Issued by the Japanese Patent Office in co-pending Japanese Patent Application No. 2009-505336 dated Mar. 24, 2011.
TIPO Search Report re: 94136438 dated Apr. 7, 2011.
Banks, R.E. et al Organofluorine Chemistry: Principles and Commercial Applications (1994) pp. 132-133.
DeGroot, J.H. et al 'Meniscal Tissue Regeneration in Porous 50/50 Copoly(1-lactide/epsilon-caprolactone) Implants' Biomaterials, Elsevier Science Publishers BV., Barking, GB, vol. 18, No. 8, Apr. 1997, pp. 613-622, XP 004058386.
A Nurse's Guide to Fibrin Sealants—Your Questions Answered http://www.cslsurgery.com/international/beriplast/nurses/pdf/NursesQuestionnaire.pdf (2014), 13 pages.
Singh, M. et al 'Biosoluble Polymers for Drug Delivery' Makromol. Chem. (1980) 181, No. 12, pp. 2433-2439.
U.S. Appl. No. 11/252,120 filed Oct. 17, 2005 'Reinforced Absorbable Multilayered Fabric for Use in Medical Devices', First named Inventor Dhanuraj S. Shetty; Examiner Norca Liz Torres Velaszquez.
U.S. Appl. No. 11/252,175 filed Oct. 17, 2005 'Reinforced Absorbable Multilayered Hemostatic Wound Dressing' First Named Inventor Anne Jessica Gorman, Examiner Kevin S. Orwig.
U.S. Appl. No. 11/400,849 filed Apr. 10, 2006, 'Reinforced Absorbable Multilayered Hemostatic Wound Dressing' First Named Inventor Anne Jessica Forman, Examiner Kevin S. Orwig.
International Preliminary Report on Patentability re: PCT/US2005/037406 dated Apr. 24, 2007.
International Preliminary Report on Patentability re: PCT/US2005/037407 dated Apr. 24, 2007.
International Preliminary Report on Patentability re: PCT/US2006/013284 dated Oct. 14, 2008.
International Search Report dated May 24, 2006 for corresponding Appln. No. PCT/US2005/037402.
International Search Report dated Jun. 7, 2006 for corresponding Appln. No. PCT/US2005/037406.
International Search Report dated Dec. 8, 2006 for corresponding Appln. No. PCT/US2006/013284.
Written Opinion for corresponding application No. PCT/US2005/037406 dated Jun. 7, 2006.
Written Opinion for corresponding application No. PCT/US2006/013284 dated Dec. 8, 2006.
Miller et al., "An Investigation of the Chemical Reactions of Oxidized Regenerated Cellulose", Experimental Medicine and Surgery (1961) 19 pp. 196-201.
Schonauer et al., "The use of local agents: bone wax, gelatin, collagen, oxidized cellulose", European Spine Journal (2004) 13 Suppl 1:S89-96.
Achneck H. et al., "A comprehensive review of topical hemostatic agents", Annals of Surgery, Feb. 2010, 251, No. 2 pp. 217-228.

* cited by examiner

Analysis of HBLT Burst Pressure (mmHg) Data
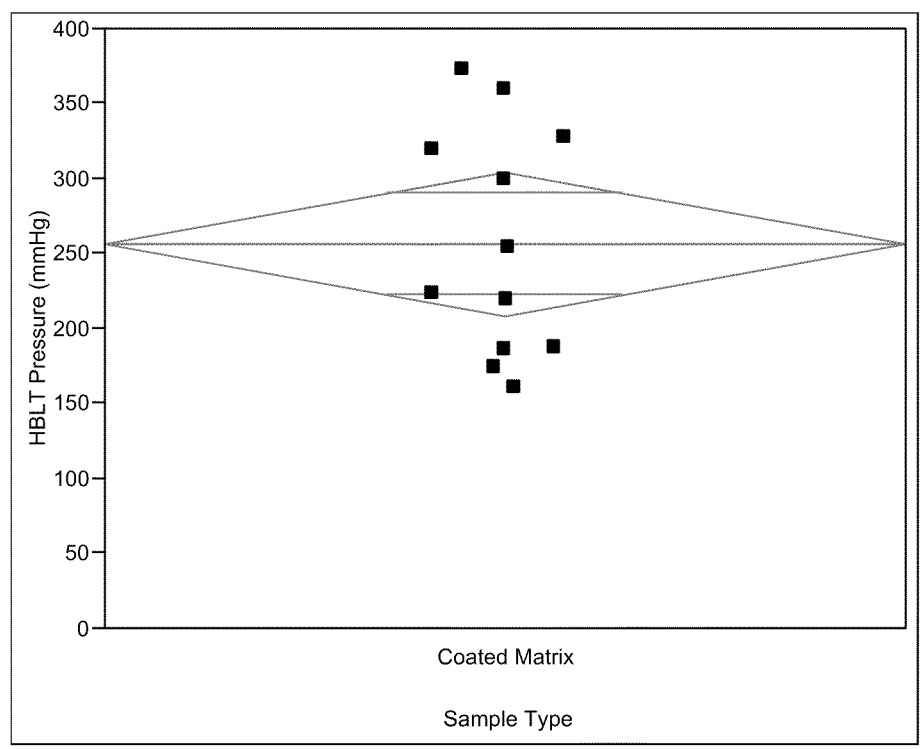

METHOD OF MAKING A REINFORCED ABSORBABLE MULTILAYERED HEMOSTATIC WOUND DRESSING

CROSS REFERENCE TO RELATED APPLICATIONS

This is a divisional of application Ser. No. 11/400,849, filed on Apr. 10, 2006, This application claims priority from U.S. Ser. No. 11/252,175 filed on 17 Oct. 2005, which claimed priority from U.S. Provisional Application Ser. No. 60/620,539, filed on 20 Oct. 2004 and U.S. Provisional Application Ser. No. 60/696,258, filed on 1 Jul. 2005.

FIELD OF THE INVENTION

The present invention relates to a reinforced absorbable multilayered hemostatic wound dressing.

BACKGROUND OF THE INVENTION

The control of bleeding as well as sealing of air and various bodily fluids is essential and critical in surgical procedures to minimize blood loss, to seal tissue and organ structures, to reduce post-surgical complications, and to shorten the duration of the surgery in the operating room.

In an effort to provide dressings with enhanced hemostatic and tissue sealing and adhering properties, therapeutic agents, including, but not limited to, thrombin, fibrin and fibrinogen have been combined with dressing carriers or substrates, including gelatin-based carriers, polysaccharide-based carriers, glycolic acid or lactic acid-based carriers and a collagen matrix. Examples of such dressings are disclosed in U.S. Pat. Nos. 6,762,336, 6,733,774 and PCT publication WO 2004/064878 A1.

Due to its biodegradability and its bactericidal, tissue sealing, tissue repairing, drug delivering and hemostatic properties, it is desirable to utilize cellulose that has been oxidized to contain carboxylic acid moieties, hereinafter referred to as carboxylic-oxidized cellulose, as a topical dressing in a variety of surgical procedures, including neurosurgery, abdominal surgery, cardiovascular surgery, thoracic surgery, head and neck surgery, pelvic surgery and skin and subcutaneous tissue procedures.

However, when carboxylic-oxidized cellulose is utilized in combination with thrombin and/or fibrinogen, the acidic moieties that may be present in the cellulose denature the activity of the thrombin and/or fibrinogen. Therefore, it is desirable to shield the and/or fibrinogen from such acid moieties to maintain their hemostatic activities.

As used herein, the term "nonwoven fabric" includes, but is not limited to, bonded fabrics, formed fabrics, or engineered fabrics, that are manufactured by processes other than, weaving or knitting. More specifically, the term "nonwoven fabric" refers to a porous, textile-like material, usually in flat sheet form, composed primarily or entirely of staple fibers assembled in a web, sheet or batt. The structure of the nonwoven fabric is based on the arrangement of, for example, staple fibers that are typically arranged more or less randomly. The tensile, stress-strain and tactile properties of the nonwoven fabric ordinarily stem from fiber to fiber friction created by entanglement and reinforcement of, for example, staple fibers, and/or from adhesive, chemical or physical bonding. Notwithstanding, the raw materials used to manufacture the nonwoven fabric may be yarns, scrims, netting, or filaments made by processes that include, weaving or knitting.

SUMMARY OF THE INVENTION

The present invention is directed to a reinforced absorbable multilayered hemostatic wound dressing comprising a first absorbable nonwoven fabric reinforced by one or more second absorbable woven or knitted fabric, and thrombin and/or fibrinogen, and method of making. More particularly, the first absorbable nonwoven fabric comprises fibers comprising aliphatic polyester polymers, copolymers, or blends thereof, while the second absorbable woven or knitted fabric comprises oxidized regenerated cellulose fibers.

BRIEF DESCRIPTION OF THE DRAWING

The FIGURE shows the pressure required to disrupt/burst the seal formed between the tissue and the hemostatic wound dressing.

DETAILED DESCRIPTION OF THE INVENTION

The multilayered dressings described herein provide and maintain effective hemostasis when applied to a wound requiring hemostasis. Effective hemostasis, as used herein, is the ability to control and/or abate capillary, venous, or arteriole bleeding within an effective time, as recognized by those skilled in the art of hemostasis. Further indications of effective hemostasis may be provided by governmental regulatory standards and the like.

In certain embodiments, multilayered dressings of the present invention are effective in providing and maintaining hemostasis in cases of severe or brisk bleeding. As used herein, severe bleeding is meant to include those cases of bleeding where a relatively high volume of blood is lost at a relatively high rate. Examples of severe bleeding include, without limitation, bleeding due to arterial puncture, liver resection, blunt liver trauma, blunt spleen trauma, aortic aneurysm, bleeding from patients with over-anticoagulation, or bleeding from patients with coagulopathies, such as hemophilia.

The reinforced absorbable multilayered dressing generally comprises a nonwoven fabric and one or more reinforcement fabric. The reinforcement fabric provides a backing to which the nonwoven fabric may be attached, either directly or indirectly, wherein thrombin and/or fibrinogen are substantially homogeneously dispersed throughout the nonwoven fabric and/or are disposed on the surface of the nonwoven fabric. The reinforcement fabric provides strength to the dressing sufficient to permit the user of the dressing to place and manipulate the dressing on or within a wound or directly onto tissue of a patient requiring hemostasis, or tissue sealing and adhering.

In addition to serving as a carrier for the thrombin and/or fibrinogen, the nonwoven fabric also serves to shield the thrombin and/or fibrinogen from acidic moieties that may be present in the reinforcement fabric, such as is the case where carboxylic-oxidized cellulose is used as the reinforcement fabric.

The nonwoven fabric functions as the first absorbable nonwoven fabric of the reinforced absorbable multilayered dressing described herein. The first absorbable nonwoven fabric is comprised of fibers comprising aliphatic polyester polymers, copolymers, or blends thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one).

Preferably, the first absorbable nonwoven fabric comprises a copolymer of glycolide and lactide, in an amount ranging from about 70 to 95% by molar basis of glycolide and the remainder lactide.

Preferably, the nonwoven fabric is made by processes other than, weaving or knitting. For example, the nonwoven fabric may be prepared from yarn, scrims, netting or filaments that have been made by processes that include, weaving or knitting. The yarn, scrims, netting and/or filaments are crimped to enhance entanglement with each other and attachment to the second absorbable woven or knitted fabric. Such crimped yarn, scrims, netting and/or filaments may then be cut into staple that is long enough to entangle. The staple may be between about 0.1 and 2.5 inches long, preferably between about 0.5 and 1.75 inches, and most preferably between about 1.0 and 1.3 inches. The staple may be carded to create a nonwoven batt, which may be then needlepunched or calendared into the first absorbable nonwoven fabric. Additionally, the staple may be kinked or piled.

Other methods known for the production of nonwoven fabrics may be utilized and include such processes as air laying, wet forming and stitch bonding.

Such procedures are generally discussed in the Encyclopedia of Polymer Science and Engineering, Vol. 10, pp. 204-253 (1987) and Introduction to Nonwovens by Albin Turbank (Tappi Press, Atlanta Ga. 1999), both incorporated herein in their entirety by reference.

The thickness of the nonwoven fabric may range from about 0.25 to 2 mm. The basis weight of the nonwoven fabric ranges from about 0.01 to 0.2 $g/in^2$; preferably from about 0.03 to 0.1 $g/in^2$; and most preferably from about 0.04 to 0.08 $g/in^2$. The weight percent of first absorbable nonwoven fabric may range from about 5 to 50 percent, based upon the total weight of the reinforced absorbable multilayered dressing having thrombin and/or fibrinogen.

The second absorbable woven or knitted fabric functions as the reinforcement fabric and comprises oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used to prepare the second absorbable woven or knitted fabric. Regenerated cellulose is preferred due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents each of which is hereby incorporated by reference as if set forth in its entirety.

Examples of fabrics that may be utilized as the reinforcement fabric include, but are not limited to, Interceed® absorbable adhesion barrier, Surgicel® absorbable hemostat; Surgicel Nu-Knit® absorbable hemostat; and Surgicel® Fibrillar absorbable hemostat; each available from Johnson & Johnson Wound Management Worldwide or Gynecare Worldwide, each a division of Ethicon, Inc., Somerville, N.J.

The reinforcement fabric utilized in the present invention may be woven or knitted, provided that the fabric possesses the physical properties necessary for use in contemplated applications. Such fabrics, for example, are described in U.S. Pat. Nos. 4,626,253, 5,002,551 and 5,007,916, the contents of which are hereby incorporated by reference herein as if set forth in its entirety. In preferred embodiments, the reinforcement fabric is a warp knitted tricot fabric constructed of bright rayon yarn that is subsequently oxidized to include carboxyl or aldehyde moieties in amounts effective to provide the fabrics with biodegradability.

In an alternative embodiment, the reinforcement fabric comprises fibers comprised of aliphatic polyester polymers, copolymers, or blends thereof alone or in combination with oxidized polysaccharide fibers.

The second absorbable woven or knitted fabric preferably comprises oxidized regenerated cellulose and may have a basis weight ranging from about 0.001 to 0.2 $g/in^2$, preferably in the range of about 0.01 to 0.1 $g/in^2$, and most preferably in the range of about 0.04 to 0.07 $g/in^2$.

The first absorbable nonwoven fabric is attached to the second absorbable woven or knitted fabric, either directly or indirectly. For example, the nonwoven fabric may be incorporated into the second absorbable woven or knitted fabric via needlepunching, calendaring, embossing or hydroentanglement, or chemical or thermal bonding. The staple of the first absorbable nonwoven fabric may be entangled with each other and imbedded in the second absorbable woven or knitted fabric. More particularly, for methods other than chemical or thermal bonding, the first absorbable nonwoven fabric may be attached to the second absorbable woven or knitted fabric such that at least about 1% of the staple of the first absorbable nonwoven fabric are exposed on the other side of the second absorbable woven or knitted fabric, preferably about 10-20% and preferably no greater than about 50%. This ensures that the first absorbable nonwoven fabric and the second absorbable woven or knitted fabric remain joined and do not delaminate under normal handling conditions. The reinforced absorbable multilayered fabric is uniform such that substantially none of the second absorbable woven or knitted fabric is visibly devoid of coverage by the first absorbable nonwoven fabric.

One method of making the multilayered fabric described herein is by the following process. Absorbable polymer fibers, having a denier per fiber of about 1 to 4, may be consolidated to about 80 to 120 denier multifilament yarn and then to about 800 to 1200 denier yarns, thermally crimped and then cut to a staple having a length between about 0.75 and 1.5 inch. The staple may be fed into a multiroller dry lay carding machine one or more times and carded into a uniform nonwoven batt, while humidity is controlled between about 20-60% at a room temperature of 15 to 24° C. For example, the uniform nonwoven batt may be made using a single cylinder roller-top card, having a main cylinder covered by alternate rollers and stripper rolls, where the batt is doffed from the surface of the cylinder by a doffer roller and deposited on a collector roll. The batt may be further processed via needlepunching or any other means such as calendaring. Thereafter, the first absorbable nonwoven fabric may be attached to the second absorbable woven or knitted fabric by various techniques such as needlepunching. The reinforced absorbable multilayered fabric may then be scoured by washing in an appropriate solvent and dried under mild conditions for 10-30 minutes.

It is desirable to control process parameters such as staple length, opening of the staple, staple feed rate, and relative humidity. For example, the consolidated yarns may have from about 5 to 50 crimps per inch and preferably from about 10 to 30 crimps per inch. Efficient cutting of the crimped yarns is desirable, as any long and incompletely cut staple tends to stick on the carding machine and cause pilling. A preferred range of the staple length is from about 0.75 to 1.5 inches, and preferably from about 1.0 to 1.3 inches.

To optimize uniformity and minimize the build-up of static electricity, the relative humidity may be controlled during batt processing, preferably during carding to form the uniform nonwoven batt. Preferably, the nonwoven batt is processed using a dry lay carding process at a relative humidity of at least about 20% at a room temperature of about 15 to 24° C. More preferably, the nonwoven batt is processed at a relative humidity of from about 40% to 60%.

The multilayered fabric is scoured using solvents suitable to dissolve any spin finish. Solvents include, but are not limited to, isopropyl alcohol, hexane, ethyl acetate, and methylene chloride. The multilayered fabric is then dried under conditions to provide sufficient drying while minimizing shrinkage.

The reinforced absorbable multilayered fabric may have an average thickness of between about 0.5 and 3.0 mm, preferably between about 1.00 and 2.5 mm, and most preferably between about 1.2 and 2.0 mm. The reported thickness is dependent upon the method of thickness measurement. Preferred methods are the ASTM methods (ASTM D5729-97 and ASTM D1777-64) conventionally used for the textile industry in general and non-woven in particular. Such methods can be slightly modified and appropriately adopted in the present case as described below. The basis weight of the reinforced absorbable multilayered fabric is between about 0.05 and 0.25 $g/in^2$, preferably between about 0.08 and 0.2 $g/in^2$, and most preferably between about 0.1 and 0.18 $g/in^2$. The reinforced absorbable multilayered fabric is uniform such that there is no more than about 10% variation (relative standard deviation of the mean) in the basis weight or thickness across each square inch.

The thrombin and/or fibrinogen may be animal derived, preferably human, or may be recombinant. The thrombin activity on the multilayered dressing may be in the range of about 20 to 500 $IU/cm^2$, preferably about 20 to 200 $IU/cm^2$, and most preferably about 50 to 200 $IU/cm^2$. The fibrinogen activity on the multilayered dressing may be in the range of about 2 to 15 $mg/cm^2$, preferably about 3 to 10 $mg/cm^2$, and most preferably about 4 to 7 $mg/cm^2$.

The basis weight of the multilayered dressing having the thrombin and/or fibrinogen powders is between 0.1 and 1.0 $g/in^2$, preferably between 0.1 and 0.5 $g/in^2$, and most preferably between 0.1 and 0.3 $g/in^2$. The multilayered dressing having the thrombin and/or fibrinogen may be sterilized, for example, by radiation, preferably by electron beam radiation.

The air porosity of the multilayered dressing having the thrombin and/or fibrinogen powders ranges from about 50-250 $cm^3/sec/cm^2$, preferably between 50-150 $cm^3/sec/cm^2$, and most preferably 50-100 $cm^3/sec/cm^2$.

When the reinforced absorbable multilayered dressing is used internally, about 50 to 75% of its mass is absorbed after about 2 weeks. The percent of mass loss may be measured by using a rat implantation model. Here the dressing is inserted into the rat by first making a midline incision (approximately 4 cm) in the skin over the lumbosacral vertebral column of a rat. The skin is then separated from the underlying connective tissue, bilaterally, to expose the superficial gluteal muscles. An incision is then made in the dorso-lateral fascia, which is located above the gluteal muscles and directly adjacent to the vertebral column. Using blunt dissection, a small pocket is created between the fascia and the gluteal muscle lateral to the incision. The multilayered dressing is placed in the gluteal pocket. The fascia is then sutured in place. After two weeks, the rat is euthanized and the multilayered dressing is explanted to determine the percent mass loss over the two week period.

The first absorbable nonwoven fabric retains solid thrombin and/or solid fibrinogen powder without separation and with minimal loss of the powder from its surface. Thrombin and/or fibrinogen containing solutions are separately lyophilized. The lyophilized materials are then ground into powders using a superfine mill or a cooled blade mill. The powders are weighed and suspended together in a carrier fluid in which the proteins are not soluble. A preferred carrier fluid is a perfluorinated hydrocarbon, including but not limited to HFE-7000, HFE-7100, HFE-7300 and PF-5060 (commercially available from 3M of Minnesota). Any other carrier fluid in which the proteins do not dissolve may be used, such as alcohols, ethers or other organic fluids. The suspension is thoroughly mixed and applied to the first absorbable nonwoven fabric via conventional means such as wet, dry or electrostatic spraying, dip coating, painting, or sprinkling, while maintaining a room temperature of about 60 to 75 degrees F. and relative humidity of about 10 to 45%. The multilayered dressing is then dried at ambient room temperature and packaged in a suitable moisture barrier container. The multilayered dressing having the thrombin and/or fibrinogen contains no more than 25% moisture, preferably no more than 15% moisture, and most preferably no more than 5% moisture.

The amount of thrombin and/or fibrinogen powder applied to the nonwoven fabric is sufficient to cover its surface such that no area is visibly devoid of coverage. The powder may sit mostly on top of the nonwoven fabric or may penetrate into the nonwoven fabric as far as the surface of the second absorbable woven or knitted fabric. However, the bulk of the powder does not contact the second absorbable woven or knitted fabric, and no more than trace amounts of the powders penetrate to the underside of the second absorbable woven or knitted fabric.

As a surgical dressing, the multilayered dressing described herein may be used as an adjunct to primary wound closure devices, such as arterial closure devices, staples, and sutures, to seal potential leaks of gasses, liquids, or solids as well as to provide hemostasis. For example, the multilayered dressing may be utilized to seal air from tissue or fluids from organs and tissues, including but not limited to, bile, lymph, cerebrospinal fluids, gastrointestinal fluids, interstitial fluids and urine.

The multilayered dressing described herein has additional medical applications and may be used for a variety of clinical functions, including but not limited to tissue reinforcement and buttressing, i.e., for gastrointestinal or vascular anastomoses, approximation, i.e., to connect anastomoses that are difficult to perform (i.e. under tension), and tension releasing. The dressing may additionally promote and possibly enhance the natural tissue healing process in all the above events. This dressing can be used internally in many types of surgery, including, but not limited to, cardiovascular, peripheral-vascular, cardio-thoracic, gynecological, neuro- and general surgery. The dressing may also be used to attach medical devices (e.g. meshes, clips and films) to tissues, tissue to tissue, or medical device to medical device.

EXAMPLE 1

Poly (glycolide-co-lactide) (PGL, 90/10 mol/mol) was melt-spun into fiber. A 80 denier multifilament yarn was consolidated into a 800 denier consolidated yarn. The consolidated yarn was crimped at approximately 110° C. The crimped yarn was cut into staple having a length of about 1.25" in length. 20 g of the crimped staple was accurately weighed and laid out uniformly on the feed conveyor belt of a multi-roller carding machine. The environmental conditions (temp: 21° C./55% RH) were controlled. The staple was then carded to create a nonwoven batt. The batt was removed from the pick-up roller and cut into 4 equal parts. These were re-fed into the carder perpendicular to the collection direction. After this second pass the batt was weighed (19.8 g: 99% fabric yield) and then compacted into a felt. The compact felt was precisely laid onto an ORC fabric and firmly attached via 2 passes in the needlepunching equipment. The multilayered fabric was trimmed and scoured in 3 discrete isopropyl alcohol baths to remove spin finish and any machine oils. The scoured multilayered fabric was dried in an oven at 70° C. for 30 minutes, cooled and weighed.

18.93 g of BAC-2 [(Omrix Biopharmaceuticals, Inc.) specific activity (by Clauss) 0.3 g/g] and 1.89 g of thrombin-containing powder (also from Omrix Biopharmaceuticals, Inc.) were mixed thoroughly with about 420 ml of HFE-7000. The slurry was sprayed through a nozzle onto the multilayered fabric weighing about 12 g and sized to 8"×12". The multilayered hemostatic wound dressing was air dried for about 30 minutes. The environmental conditions were maintained at 24° C./45% RH throughout the process. The multilayered hemostatic wound dressing was cut into appropriate sizes and packed in a tray. The tray is specifically designed such that the clearance between the top and the bottom of the tray is slightly less than the overall thickness of the dressing to ensure minimized motion of the dressing during shipping and handling, to prevent the coated powder from dislodging during transit. The tray is further packaged in a foil pouch, which is thermally sealed with dessicants as needed. The dressing was stored at 2-8° C. until needed.

The "thickness" of the multilayered fabric/dressing was measured as described herein. The measurement tools were:

(1) Mitutoyo Absolute gauge Model number ID-C125EB [Code number—543-452B]. The 1" diameter foot was used on the gauge.

(2) A magnetic holder was used to lock in place and set the caliper up to the die platen.

(3) Two metal plates ~2.75"×2"×0.60", weighing between 40.8 g to 41.5 g [combined total of ~82.18 g].

The multilayered fabric/dressing was placed on a platen surface that is a smooth and machined surface. The two metal plates were placed on top of each other on the multilayered fabric/dressing and gently pressed at their corners to make sure the multilayered fabric/dressing is flat. The gauge foot was placed onto the top of the metal plates and was then re-lifted and re-placed, at which time a reading was made.

EXAMPLE 2

In general, anesthetized pigs were dissected to expose the abdominal aorta. A biopsy punch was used to remove a 4 mm section of the aorta. The blood was allowed to flow freely, and the dressing to be tested was quickly applied to the wound site while aspirating any excessive pooling blood. Manual pressure was applied to hold the dressing to the wound site for 3 minutes. At the end of the three-minute period, pressure was removed. The test was considered a "pass" if the dressing adhered well to the wound and achieved full hemostasis with no re-bleeding.

| Sample ID | Thrombin Activity (IU/cm²) | Fibrinogen Activity (mg/cm²) | Hemostatic Performance-Porcine Aortic Punch |
|---|---|---|---|
| 1 | ~50 | 4.86 | Pass |
| 2 | ~50 | 6.23 | Pass |
| 3 | ~50 | 5.36 | Pass |
| 4 | ~50 | 5.49 | Pass |
| 5 | ~50 | 6.19 | Pass |
| 6 | ~50 | 7.80 | Pass |
| 7 | ~50 | 7.90 | Pass |
| 8 | ~50 | 6.77 | Pass |
| 9 | ~50 | 6.97 | Pass |
| 10 | ~50 | 3.31 | Fail |
| 11 | ~50 | 5.99 | Pass |
| 12 | ~50 | 5.89 | Pass |
| 13 | ~50 | 8.52 | Pass |
| 14 | ~50 | 7.11 | Pass |
| 15 | ~50 | 11.07 | Fail |
| 16 | ~50 | 12.47 | Pass |
| 17 | ~50 | 8.43 | Pass |
| 18 | ~50 | 11.77 | Fail |
| 19 | ~50 | 8.61 | Fail |
| 20 | ~50 | 8.70 | Pass |
| 21 | ~50 | 8.52 | Fail |
| 22 | ~50 | 6.50 | Pass |
| 23 | ~50 | 6.68 | Pass |
| 24 | ~50 | 9.13 | Fail |
| 25 | ~50 | 7.68 | Pass |
| 26 | ~50 | 6.59 | Pass |
| 27 | ~50 | 7.03 | Pass |
| 28 | ~50 | 7.55 | Pass |
| 29 | ~50 | 6.85 | Pass |
| 30 | ~50 | 5.0-10.0*** | pass |
| 31 | ~50 | 5.0-10.0*** | pass |
| 32 | ~50 | 5.0-10.0*** | pass |
| 33 | ~50 | 5.0-10.0*** | pass |
| 34 | ~50 | 5.0-10.0*** | pass |
| 35 | ~50 | 5.0-10.0*** | pass |
| 36 | ~50 | 5.0-10.0*** | pass |
| 37 | ~50 | 5.0-10.0*** | fail* |
| 38 | ~50 | 5.0-10.0*** | fail* |
| 39 | ~50 | 5.0-10.0*** | pass |
| 40 | ~50 | 5.0-10.0*** | pass |
| 41 | ~50 | 5.5-7.5 | pass |
| 42 | ~50 | 5.5-7.5 | pass |
| 43 | ~50 | 5.5-7.5 | fail* |
| 44 | ~50 | 5.5-7.5 | fail* |
| 45 | ~50 | 5.5-7.5 | fail** |
| 46 | ~50 | 5.5-7.5 | pass |
| 47 | ~50 | 5.5-7.5 | pass |
| 48 | ~50 | 5.5-7.5 | pass |

*Failure occurred due to inadequate aspiration of pooling blood at the puncture site
**Failure occurred due to inadequate aspiration of pooling blood at the puncture site as a result of suction hose failure
***Targeted range during production All animals were euthanized after conclusion of the test, except for Sample ID 46 and 47, which survived for at least 2 weeks post surgery.

EXAMPLE 3

Non-Woven PGL Fabric with ORC Reinforcement Fabric

Poly (glycolide-co-lactide) (PGL, 90/10 mol/mol) was melt-spun into fiber. The fiber was cut into small staple and then carded to create a very fine nonwoven fabric of about 1.25 millimeters thick and had a density of about 98.1 mg/cc. The nonwoven fabric was then needle punched into a knitted carboxylic-oxidized regenerated cellulose fabric, available from Ethicon, Inc., under the tradename Interceed®, to secure the nonwoven fabric to the ORC fabric. The final construct comprised about 60 weight percent of the nonwoven fibers.

EXAMPLE 4

Analysis of Adhesive/Sealant Properties of Samples Coated with Fibrinogen and Thrombin The material described in Example 3 was coated with dry particles consisting mostly of fibrinogen (7 to 8 mg/cm$^2$) and thrombin (50 IU/cm$^2$), and then tested using a Hydraulic Burst Leak Test (HBLT). Samples were cut into circular pieces of ¾ inch diameter. The samples were placed onto a tissue substrate derived from bovine pericardium with a hole in the center of the tissue. The pierced tissue substrate was placed over an airtight chamber into which saline was pumped. The pressure required to disrupt/burst the seal formed between the tissue and the sample was measured (see FIG. 1). Samples without protein coating do not adhere to the tissue.

EXAMPLE 5

Poly (glycolide-co-lactide) (PGL, 90/10 mol/mol) was melt-spun into fiber. A 80 denier multifilament yarn was consolidated into a 800 denier consolidated yarn. The consolidated yarn was crimped at approximately 110° C. The crimped yarn was cut into staple having a length of about 1.25" in length. 44 g of the crimped staple was accurately weighed after conditioning the yarn for about 30 minutes in a high humidity environment (>55% RH). The yarn was laid out uniformly on the feed conveyor belt of a multi-roller carding machine. The feed time (5 minutes) was accurately controlled to within 30-45 seconds. The environmental conditions (temp: 21° C./25% RH) were recorded. Static bars were employed near the 2$^{nd}$ Randomiser roller as well as near the steel pick up roller and were turned on during the run to minimize the detrimental impact of static generation on the uniformity and yield of the resulting batt. The staple was then carded to create a nonwoven batt. Two vacuum inlets were strategically placed near the two edges of the 2$^{nd}$ Randomizer roller to control the width of the ensuing batt. The batt was removed from the pick-up roller and weighed (41 g: 91% yield). The uniform batt was precisely laid onto an ORC fabric and firmly attached via a single pass in the needlepunching equipment. The needle penetration depth was controlled at 12 mm. The multilayered fabric was trimmed and scoured on a rack (along with other similarly produced sheets) suspended in a tank containing isopropyl alcohol to remove spin finish and any machine oils. The scoured multilayered fabric (matrix sheet) was calendered to remove excess solvent and dried in an oven at 70° C. for app. 30 minutes, cooled and weighed.

EXAMPLE 6

The matrix sheet as described has an off-white/beige color on both sides. One side may be described as the non-woven side where as the other side as the knitted fabric side. For certain application, it may be vital to identify the non-woven versus knitted surfaces of the matrix. Under difficult environmental conditions, the similarity in color and texture (to some extent) makes it difficult to identify one side from the other. Several means were employed to impart sidedness to the matrix sheet, which enables the observer to distinguish the 2 sides apart. These means include physical (stitching/knitting, braiding, pleating, etc), thermo-mechanical (heat, heat embossing; laser etching; etc) and chromic (use of a dye) means may be employed to achieve sidedness. The following examples describe some of the means:

6a) The matrix sheet was modified on the knitted fabric side by attaching a 1 mm wide 4 inch long braided tape of the polyglactin 910 fiber. The tapes although successful in imparting sidedness add to the amount of the longer resorbing Polyglactin 910.

6b) A web made of dyed nylon fiber was placed under the knitted fabric and the non-woven batt during the needle-punching step. The web is secured to the knitted fabric side due to the needling process. The web affords excellent sidedness and if available in an absorbable material, could be used to make completely resorbable, implantable matrix sheets. The web (mesh) can be secured similarly on the non-woven side. Other means of securing the web may be thermo-mechanical in nature. Inclusion of such a web can be for the reason of mechanical enforcement as well. In such cases the web could be secured on either side or even between the two layers. Such a reinforced structure may have multiple applications.

6c) The small amount of Polyglactin 910 that resides on the knitted fabric side (due to the needle-punching step) of the matrix sheet can be thermally modified to create sidedness. This can include heating under pressure such that a shiny film of Polyglactin 910 is formed. Other options include heat embossing a discernible pattern. Both approaches achieve sidedness but may result in thermal degradation of the polymer/construct 6d). The knitted ORC fabric, prior to the needle-punching step is pleated (vertical or horizontal pleats). The pleats are stabilized by using heat and pressure. The pleated fabric is then used in place of the regular fabric for the rest of the process as described in Example 5. The resulting matrix sheet has distinct stripes that achieve the sidedness.

6 e) Dyed Polyglactin 910 creates matrix sheet that is colored on the non-woven side and off-white/beige on the other. This construct achieves sidedness. A dye can be used similarly by employing a dyed suture thread etc. on the knitted side. The suture (braided into a tape or used as is) may be sewed in or thermally bonded.

While the examples demonstrate certain embodiments of the invention, they are not to be interpreted as limiting the scope of the invention, but rather as contributing to a complete description of the invention. All reinforcement fabrics described in the examples below are the nonsterile materials of the corresponding commercial products referred by their tradenames.

The invention claimed is:

1. A method for making a multilayered wound dressing having a first absorbable nonwoven fabric that comprises fibers comprised of aliphatic polyester polymers or copolymers of one or more monomers selected from the group consisting of lactic acid, lactide, glycolic acid, glycolide, ε-caprolactone, p-dioxanone, and trimethylene carbonate; one or more second absorbable woven or knitted fabric that comprises oxidized polysaccharides; thrombin and fibrinogen, comprising the steps of:
   (a) crimping absorbable polymer fibers or yarns in the range of about 10 to 30 crimps per inch;
   (b) cutting the crimped fibers or yarns to a staple length between about 0.1 and 2.5 inch;
   (c) carding the staple to form the first absorbable nonwoven fabric;
   (d) attaching the first absorbable nonwoven fabric to the second absorbable woven or knitted fabric to form a multilayered wound dressing;
   (e) applying thrombin and fibrinogen as a suspension in a liquid carrier onto the first absorbable nonwoven fabric, wherein said liquid carrier is a perfluorinated hydrocarbon in which thrombin and fibrinogen are not soluble, and;

(f) drying said multilayered wound dressing.

2. The method of claim 1, wherein the humidity of the environment for step (c) is from about 40 to 60%, at a room temperature of about 15 to 24° C.

3. The method of claim 1, where the first absorbable nonwoven fabric comprises glycolide/lactide copolymer.

4. The method of claim 1, where the second absorbable woven or knitted fabric comprises oxidized cellulose.

5. The method of claim 4, where the second absorbable woven or knitted fabric comprises oxidized regenerated cellulose.

6. The method of claim 4, where the second absorbable woven or knitted fabric is an absorbable knitted fabric comprising oxidized regenerated cellulose.

7. The method of claim 1, where the first absorbable nonwoven fabric comprises glycolide/lactide copolymer, and the second absorbable woven or knitted fabric comprises oxidized regenerated cellulose.

8. The method of claim 7, where the first absorbable nonwoven fabric comprises staple having a length from about 0.75 to 1.5 inches.

9. The method of claim 7, where the first absorbable nonwoven fabric comprises staple having a length from about 1.0 to 1.3 inches.

10. The method of claim 7, where the first absorbable nonwoven fabric comprises a copolymer of glycolide and lactide, in an amount ranging from about 70 to 95% by molar basis of glycolide and the remainder lactide, and the second absorbable woven or knitted fabric comprises oxidized regenerated cellulose.

11. The method of claim 9, where the staple is derived from fiber of about 1 to 4 denier per filament.

12. The method of claim 7, where the first absorbable nonwoven fabric has a basis weight of about 0.01 to 0.2 $g/in^2$; the second absorbable woven or knitted fabric has a basis weight of about 0.001 to 0.2 $g/in^2$; and the multilayered dressing having the thrombin and/or fibrinogen thereon has a basis weight of about 0.1 and 1.0 $g/in^2$.

13. The method of claim 7, wherein the thrombin activity on the multilayered dressing ranges from about 20 to 500 $IU/cm^2$, and the concentration of fibrinogen on the multilayered dressing ranges from about 2 to 15 $mg/cm^2$.

14. The method according to claim 1, further comprising the step of sterilizing the multilayered wound dressing.

15. The method according to claim 14, wherein the multilayered wound dressing is sterilized by radiation.

16. The method according to claim 14, wherein the multilayered wound dressing is sterilized by electron beam radiation.

17. The method of claim 1, wherein the step (e) is performed while maintaining a room temperature of about 60 to 75 degrees F.

18. The method of claim 17, wherein the step (e) is performed while maintaining a relative humidity of about 10 to 45%.

19. The method of claim 1, wherein step (f) is performed at ambient room temperature following step (e).

20. The method of claim 13 wherein the fibrinogen concentration on the resulting wound dressing after drying in step (f) is between about 4.9 and 12.5 $mg/cm^2$.

* * * * *